(12) United States Patent
Tengler et al.

(10) Patent No.: US 8,840,924 B2
(45) Date of Patent: Sep. 23, 2014

(54) COMPOSITIONS AND METHODS OF MAKING RAPIDLY DISSOLVING IONICALLY MASKED FORMULATIONS

(75) Inventors: Mark Tengler, Colleyville, TX (US); Russell McMahen, Flower Mound, TX (US)

(73) Assignee: NEOS Therapeutics, LP, Grand Prairie, TX (US)

( * ) Notice: Subject to any disclaimer, the term of this patent is extended or adjusted under 35 U.S.C. 154(b) by 228 days.

(21) Appl. No.: 12/717,251

(22) Filed: Mar. 4, 2010

(65) Prior Publication Data

US 2010/0278901 A1 Nov. 4, 2010

Related U.S. Application Data

(63) Continuation of application No. 11/255,555, filed on Oct. 21, 2005, now abandoned.

(51) Int. Cl.
*A61K 9/20* (2006.01)
*A61K 9/26* (2006.01)
*A61K 9/46* (2006.01)
*A61K 47/48* (2006.01)
*A61K 9/00* (2006.01)
*A61K 31/785* (2006.01)

(52) U.S. Cl.
CPC ......... *A61K 9/0056* (2013.01); *A61K 47/48184* (2013.01); *A61K 31/785* (2013.01)
USPC ............ 424/466; 424/464; 424/468; 424/469

(58) Field of Classification Search
None
See application file for complete search history.

(56) References Cited

U.S. PATENT DOCUMENTS

| | | | |
|---|---|---|---|
| 2,990,332 A | | 6/1961 | Keating |
| 3,594,470 A | * | 7/1971 | Borodkin et al. ............. 424/483 |
| 4,959,219 A | * | 9/1990 | Chow et al. ................... 424/480 |
| 5,674,533 A | | 10/1997 | Santus et al. |
| 5,980,945 A | | 11/1999 | Ruiz |
| 6,120,787 A | | 9/2000 | Gustafsson et al. |
| 6,596,311 B1 | * | 7/2003 | Dobetti .......................... 424/464 |
| 6,613,358 B2 | | 9/2003 | Randolph et al. |
| 7,118,765 B2 | * | 10/2006 | Norman et al. ............... 424/489 |
| 7,749,533 B2 | | 7/2010 | Fu et al. |
| 8,008,378 B2 | | 8/2011 | Hargens et al. |
| 2003/0170310 A1 | * | 9/2003 | Wadhwa ........................ 424/486 |
| 2004/0228830 A1 | | 11/2004 | Hirsh et al. |
| 2005/0036977 A1 | | 2/2005 | Gole et al. |
| 2005/0181050 A1 | * | 8/2005 | Hirsh et al. .................... 424/469 |
| 2005/0281875 A1 | | 12/2005 | Srinvasan et al. |
| 2006/0115529 A1 | * | 6/2006 | Jeong et al. .................... 424/464 |
| 2006/0193877 A1 | * | 8/2006 | Tengler et al. ................ 424/400 |
| 2007/0202167 A1 | * | 8/2007 | Srinivasan et al. ............ 424/468 |
| 2010/0092564 A1 | | 4/2010 | Park et al. |

OTHER PUBLICATIONS

CODEPREX (Chlorpheniramine Polistirex; Codeine Polistirex) Drug Information, "Drugs-About.com" (2004).
Jeong, U.S. Appl. No. 60/624,959, filed Nov. 4, 2004.
Park, U.S. Appl. No. 60/468,449, filed May 7, 2003.
Center for Drug Evaluation and Research (CDER), "Guidance for Industry: Orally Disintegrating Tablets," US Department of Health and Human Services, Food and Drag Administration (Dec. 2008), pp. 1-3.

* cited by examiner

*Primary Examiner* — Susan Tran
(74) *Attorney, Agent, or Firm* — Hunton & Williams LLP

(57) ABSTRACT

The present invention includes compositions and methods for reduce the taste of the drug in the drug resin complex. The composition may include one or more drug-resin complexes and a highly compressible, free-flowing pharmaceutical excipient. The resin is present in an amount effective to reduce the taste of the drug in the drug resin complex relative to an otherwise identical pharmaceutical composition without the resin; and wherein the highly compressible, free-flowing pharmaceutical excipient causes release of the drug-resin complex in the mouth.

25 Claims, No Drawings

COMPOSITIONS AND METHODS OF MAKING RAPIDLY DISSOLVING IONICALLY MASKED FORMULATIONS

CROSS-REFERENCE TO RELATED APPLICATION

This application is a Continuation of U.S. application Ser. No. 11/255,555 filed Oct. 21, 2005 now abandoned, the disclosure of which is herein incorporated by reference in its entirety.

FIELD OF INVENTION

The invention relates to compositions and methods of making rapidly disintegrating or chewable, sustained-release formulations, and more particularly, to compositions and methods for making rapidly disintegrating ionically masked formulations.

BACKGROUND OF THE INVENTION

Without limiting the scope of the invention, its background is described in connection with ionically masked pharmaceutical agents that are rapidly disintegrating and delivered in an extended or sustained-release form, as an example.

Methods for sustained release are known in the art. One such method of making sustained release particles is taught in U.S. Pat. No. 6,120,787, issued to Gustafsson, et al., which teach a method for preparing parenterally administrable sustained release microparticles. The method includes preparing core particles in an aqueous medium that is essentially free from organic solvent and the biologically active substance is entrapped therein during or after preparation, e.g., drying the core particles. The coating may be the same release-controlling polymer, which is added by an air suspension technique to create a shell on the core particles without any detrimental exposure of the active substance to organic solvent.

Another sustained-release composition includes an amorphous polymer as taught in U.S. Pat. No. 6,613,358, issued to Randolph, et al., which provides for a sustained release composition of a pharmaceutical substance that includes: a biocompatible polymer that is highly amorphous and a pharmaceutical substance in a hydrophobic ion complex with an amphiphilic material. A compressed antisolverit method for manufacturing the composition it also taught, as are various product forms incorporating the composition and various uses for the composition.

Yet another sustained release drug formulation is taught in U.S. Pat. No. 5,980,945, issued to Ruiz in which a sustained release drug formulation includes a drug; a biodegradable polymer that is insoluble in water; and an oil vehicle in which both the drug and the polymer are dissolved. The oil vehicle may contain 10-100% by volume of a pharmaceutically acceptable oil and 0-90% by volume of a pharmaceutically acceptable liquid carrier for the drug or the polymer.

Finally, U.S. Pat. No. 5,674,533 issued to Santus, et al., teaches pharmaceutical compositions for the controlled release of the anti-tussive, moguisteine, in a liquid suspension designed either as ready-to-use and time-stable liquid formulations with a shelf-life of at least two years, or as dry formulations that are reconstituted with water when needed and then remain stable throughout the treatment period. Santus teaches the use of coated microgranules for the controlled release of moguisteine having sizes ranging from 50 to 500 μm, preferably from 90 to 300 μm, which are capable of remaining easily in suspension in a liquid for extended times. The microgranules have a moguisteine core, with one or more optional plasticizers and excipients, granulated into microgranules having sizes smaller than 500 uniform surfaces, substantially spherical shapes, apparent densities of about 500 to 600 g/l and very low friabilities, which are made by wet-kneading micronised moguisteine using water or a mixture of water and other solvents. These initial microgranules have controlled-release properties by, a first coating having essentially hydrophilic characteristics, which isolates the microgranules; followed by a second coating having lipophilic characteristics on top of the first coating; and a third coating having hydrophilic characteristics.

Orally administered drug formulations may be provided to the patient in many dosage forms, including solid forms (e.g., capsules, caplets, effervescent or tablets) and liquid forms (e.g., solutions, syrups, emulsions or suspensions). Generally, orally administered drug formulations administered in solid dosage form are intended to be swallowed whole and any disagreeable taste can be easily masked with an exterior coating. However, some formulations are designed for rapid absorption of the active ingredient through the oral mucosa, e.g., chewing of the tablets, effervescent, and the like and thus result in tastes that are more difficult to mask. A growing market for these and other products is the pediatric and geriatric patients.

Many pharmaceutical compositions must be formulated as liquids for use by pediatric, geriatric patients, disabled persons, incapacitated patients and persons with dysphagia often have trouble swallowing. To alleviate this challenge a number of drug delivery protocols have been developed including rapid in-mouth disintegrating tablets, tablets which disintegrate in liquid prior to ingestion, liquids and syrups, gums and transdermal compositions. Unfortunately, these delivery methods can pose their own problems.

For example, immediate release compositions with rapid absorption of the active ingredient through the oral mucosa (e.g., rapid in-mouth disintegrating tablets, tablets that disintegrate in liquid prior to ingestion, liquids and syrups, gums) may have an unpleasant texture or even an unpalatable taste associated with the immediate release agent or other component of the composition.

SUMMARY OF THE INVENTION

The present inventors recognized that certain drugs produce an unpalatable taste associated with the immediate release agent that are not effectively masked by traditional taste masking techniques. The present invention addresses the problems associated with the delivery of one or more active agents in a solid dosage form under controlled conditions. Solid, chewable formulations are often preferred by many users due to the easy of delivery, namely, natural chewing and swallowing thereby leading to increased compliance with dosing regimens. Many children and adults fail to comply with dosing instructions due to the size, shape, taste and/or mouth-feel of, e.g., tablets, caplets and even gelcaps.

The present inventors further recognized that delivery of agents in a chewable formulation is not always preferred by users because of the taste and/or mouth feel of the active agents and/or excipients often included with chewable formulations. What is needed are formulations that are manufactured using commonly used equipment, are shelf-stable have improved mouth-feel (e.g., less grainy, bitter or slimy) and provide actual controlled, sustained, mixed or modified release. Finally, it was recognized that despite many decades of research and development, controlled-release formulations have not been amenable to large-scale production in facilities and to amounts that are permissible for industrial applicability of controlled-release chewable formulations. However, despite the many known techniques for eliminating the problems commonly associated with the manufacture of chewable formulations, and hence their widespread failure, none of these formulations have solves the problems of patient compliance due to taste and mouthfeel.

More particularly, the present invention includes compositions and methods for preparing a chewable, controlled-release formulation by blending one or more controlled release microbeads having one or more active agents with one or more microbeads. The one or more microbeads may include an enteric coat, a resin coat, a lacquer coat, a pH-sensitive coating, a biodegradable polymer matrix, a water soluble matrix, an ionic matrix, combinations and mixtures thereof. The one or more microbeads may also include one or more polymers selected from cellulose, ethylcellulose, methylcellulose, propylcellulose, methoxypropylcellulose, cellulose nitrate, poly(vinyl alcohol), poly(vinyl chloride), polystyrene, polyethylene, polypropylene, poly(ethylene-co-vinyl acetate), poly(hydroxybutyric acid), poly(hydroxyvalerianic acid-co-hydroxybutyric acid), poly(lactic acid), poly(glycolic acid), poly(lactic acid-co-glycolic acid), poly(ε(-caprolactones), poly(ε-caprolactone-co-DL-lactic acid), poly(maleic anhydride), polyamides, gelatin, chitosan, collagen, poly(hydroxyalkyl)-L-glutamines, poly(γ-ethyl-L-glutaminate-co-glutamic acid), poly(L-leucine-co-L-aspartic acid), poly(proline-co-glutamic acid), poly(alkyl 2-cyanoacrylates), polyurethanes, poly(methyl methacrylate), poly(methyl methacrylate-co-methacrylic acid) and poly(methacrylate-co-hydroxypropyl methacrylate), polystyrene, polistirex, polacrilex and salts, combinations and mixtures thereof.

The present invention may be, e.g., a taste-masked soluble chewable pseudoephedrine and chlorpheniramine pharmaceutical composition. The composition includes a pseudoephedrine-resin complex, a chlorpheniramine-resin complex and one or more amorphous sugars. The composition may be a compressible, free-flowing, pharmaceutical, taste-masking excipient, wherein the highly compressible, free-flowing pharmaceutical excipient aids the release of the drug-resin complex in the mouth.

The present invention provides a method of masking the taste of a rapidly disitegrating or chewable, taste-masked pharmaceutical composition by adding one or more amorphous sugars to a pharmaceutically active drug-resin complex. A taste-masked soluble chewable composition may include pseudoephedrine and chlorpheniramine in a therapeutically effective amount formed into a pharmaceutical composition. The composition may include a pseudoephedrine-resin complex, a chlorpheniramine-resin complex, one or more amorphous sugars and a compressible, free-flowing, pharmaceutical, taste-masking excipient. The pseudoephedrine and the chlorpheniramine are slowly released as the composition is chewed. The composition becoming thixotropic when chewed but not fully dissolving for at least 10 seconds, so as to dissolve thereafter in saliva during chewing.

The present invention includes a rapidly dissolving, taste-masked hyoscyamine pharmaceutical composition. The composition includes a hyoscyamine-resin complex, one or more amorphous sugars and a compressible, free-flowing, pharmaceutical, taste-masking excipient. The hyoscyamine is released slowly when the tablet disintegrates or is chewed. The rapidly disintegrating, taste-masked pharmaceutical composition may include any salt of hyoscyamine, e.g., an ionically bound hyoscyamine. The composition may be a hyoscyamine-resin complex and one or more amorphous sugars. The hyoscyamine is released slowly when the composition is chewed, the composition becoming thixotropic when chewed but not fully dissolving for at least 30 seconds when chewed, and the composition slowly dissociates when chewed, to substantially dissociate thereafter in saliva during chewing.

The present invention includes a chewable tablet in which a pharmaceutically active drug-resin complex is slowly released when the tablet is chewed. As the tablet is chewed it becomes thixotropic but not fully dissociated for at least 10 seconds. The tablet may slowly dissociate thereafter in saliva during chewing or once swallowed for up to 24 hours. The chewable formulation may include a portion of the one or more beads with an immediate release profile and another portion with a controlled or delayed release profile. In one example, the active agent may be included in two different salt forms or on two different resins, wherein the active agent is differentially released or becomes dissolved and/or bioavailable at a different rate from the second salt or released from the second bead. When using an ion-exchange matrix, bead or resin to retain the one or more active agents the liquid solution will in some cases be a low-ionic strength, depending on the nature of the ion-exchange matrix and the one or more active agents. Based on the present disclosure, the skilled artisan may easily deter mine the best matrix for a particular active, determine the amount of loading (theoretical and empirical), and the conditions for retention and release.

Examples of active agents that may be provided as part of the chewable formulations of the present invention include vitamins, minerals, nutritional supplements, herbal extracts, gums, gels, oils, salts, mixtures and combinations thereof. Pharmaceutical active agents may include, e.g., protein, peptide, carbohydrate, polysaccharide, glycoprotein, lipid, hormone, growth factor, cytokine, interferon, receptor, antigen, allergen, antibody, antiviral, antifungal, antihelminthic, substrate, metabolite, cofactor, inhibitor, drug, nutrient, toxin, poison, explosive, pesticide, chemical warfare agent, biowarfare agent, biohazardous agent, infectious agent, prion, radioisotope, vitamin, heterocyclic aromatic compound, carcinogen, mutagen, narcotic, amphetamine, barbiturate, hallucinogen. In some cases the chewable may be, eg., a vaccine for against a virus, bacterium, helminth and/or fungi, fragments, receptors or toxins thereof, e.g., *Salmonella, Streptococcus, Brucella, Legionella, E. coli, Giardia, Cryptosporidium, Rickettsia*, spore, mold, yeast, algae, amoebae, dinoflagellate, unicellular organism, pathogen, cell, combinations and mixtures thereof. The one or more active agents may be a pharmaceutical agent, an enzyme, a cytokine, a growth promoting agent, an antibody, an antigen, a hormone, a vaccine, a cell, a live-attenuated pathogen, a heat-killed pathogen, a virus, a bacteria, a fungi, a peptide, a carbohydrate, a nucleic acid, a lipid, mixtures and combinations thereof.

Specific examples of active agents include: steroids, respiratory agents, sympathomimetics, local anesthetics, antimicrobial agents, antiviral agents, antifungal agents, antihelminthic agents, insecticides, antihypertensive agents, antihypertensive diuretics, cardiotonics, coronary vasodilators, vasoconstrictors, β-blockers, antiarrhythmic agents, calcium antagonists, anti-convulsants, agents for dizziness, tranquilizers, antipsychotics, muscle relaxants, drugs for Parkinson's disease, respiratory agents, hormones, non-steroidal hormones, antihormones, vitamins, antitumor agents, miotics, herb medicines, herb extracts, antimuscarinics, interferons, immunokines, cytokines, muscarinic cholinergic blocking agents, mydriatics, psychic energizers, humoral agents, antispasmodics, antidepressant drugs, anti-diabetics, anorectic drugs, anti-allergenics, decongestants, expectorants, antipyretics, antimigrane, anti-malarials, anti-ulcerative, anti-estrogen, anti-hormone agents, anesthetic agent, or drugs having an action on the central nervous system. For example, for use in the treatment of cold/cough symptoms the active agents may include one or more antihistamines, antitussives, expectorants and the like, e.g., hyoscyamine, pseudoephedrine, chlorpheniramine, dextromethorphan, guaifenesin, and salts thereof or mixtures of salts thereof. The chewable formulation may also include an analgesic or even a narcotic.

Examples of carriers for the actives of the present invention include any degradable, partially degradable or non-degradable and generally biocompatible polymer, e.g., polystirex, polypropylene, polyethylene, polacrilex, poly-lactic acid (PLA), poly-glycolic acid (PGA) and/or poly-lactic polyglycolic acid (PGLA) in the form or a matrix or even a bead.

The present invention also includes those chewable formulations made by the methods disclosed and claimed herein. For example, specific chewable formulation may include one or more active agents available for immediate, modified and/or extended or controlled release for use in treating cold/cough/allergy symptoms. The one or more actives for cold/cough/allergy may include one or more of the following: anti-tussives, anti-histamines, expectorants and analgesics. For example, the actives may include hyoscyamine, pseudoephedrine, chlorpheniramine, dextromethorphan, guaifenesin, and salts thereof or mixtures of salts thereof.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Pharmaceutically active agents can be administered to the patient in many forms with oral administration being the most popular as liquid solutions, emulsions, suspensions or in solid form such as capsules or tablets. The oral administration is problematic for some individual (e.g., infants, children and older persons) that are unable to swallow whole tablets and capsules. Therefore, it is desirable to administer doses in a liquid form, a dissolvable form, a chewable form or in a form that are absorbed through the oral mucosa.

Unlike tablets or capsules which are intended to be swallowed whole, forms that are absorbed through the oral mucosa must be formulated to take into account the taste of the active ingredient. Some therapeutic agents can cause strong negative sensory perceptions in the mouth due to their delivery through the mucosa. Often the sensory perceptions are so objectionable that a patient stops taking the medicine. In such cases, the use of conventional sweetener/flavor approach is not sufficient to mask or hide these negative perceptions. Conventional sweeteners and/or flavors are commonly used to prevent the taste from being apparent during the time that the medicine is in the mouth.

The present invention may be used to taste-mask a wide range of chemicals in a formulation depending on the predominant, secondary and tertiary taste. The selection of two, three or more masking agents may be modified, without undue experimentation, by comparing the most common predominant, secondary and tertiary flavors or taste of the one or more actives. Differences may also be determined between children and adults (e.g., changes in sweetness thresholds), males and females and in accordance with the flavor of the final composition (e.g., cherry versus grape).

The sense of taste caused by the excitation of taste receptors on the tongue. The tongue includes receptors for a large number of specific chemicals have been identified that contribute to the reception of taste, e.g., chemicals as sodium, potassium, chloride, glutamate and adenosine. Despite this complexity, five types of tastes are commonly recognized: Salty, Sour, Sweet, Bitter and Umami. The umami taste is that of monosodium glutamate and has recently been recognized as a unique taste, as it cannot be elicited by any combination of the other four taste types. Glutamate is present in a variety of protein-rich foods, and particularly abundant in aged cheese.

The perception of taste may also be influenced by thermal stimulation of the tongue. For example, in some people, warming the front of the tongue produces a clear sweet sensation, while cooling leads to a salty or sour sensation. Tastes are based on human sensations and some physiologists believe that each animal probably has its own perception of taste.

As used herein, the terms "extended release," "sustained release," and "delayed release" are used to define a release profile to effect delivery of an active over an extended period of time, defined herein as being between about 60 minutes and about 2, 4, 6, 8 or even 12 hours. Extended release may also be defined functionally as the release of over 80 to 90 percent (%) of the active ingredient after about 60 minutes and about 2, 4, 6 or even 8 hours. Extended release as used herein may also be defined as making the active ingredient available to the patient or subject regardless of uptake, as some actives may never be absorbed by the animal. Various extended release dosage forms may be designed readily by one of skill in art as disclosed herein to achieve delivery to both the small and large intestines, to only the small intestine, or to only the large intestine, depending upon the choice of coating materials and/or coating thickness.

As used herein, the term "USP" is used to describe the United States Pharmacopoeia a widely recognized organization that sets some of the standards that pharmaceutical manufacturers must meet to sell their drugs and drug compounds in the United States. USP standards include procedures for the physical tests that must be performed on drugs and drug compounds to ensure compliance with the specific requirements set forth within these standards.

As used herein, the term "pharmaceutically acceptable salts" is used to describe those salts in which the anion (or cation) does not contribute significantly to the toxicity or pharmacological activity of the salt, and, as such, they are the pharmacological equivalents of the bases of the compounds to which they refer. Examples of pharmaceutically acceptable acids that are useful for the purposes of salt formation include but are not limited to hydrochloric, hydrobromic, hydroiodic, citric, acetic, benzoic, mandelic, fumaric, succinic, phosphoric, nitric, maleic, mucic, isethionic, palmitic, tannic and others. The active salt combinations of the pharmacologic ingredients may be the free acids, bases or as salts having anionic functional groups such as bitartrate, maleate, citrate, chloride, bromide, acetate and sulfate. The source of the functional groups may be natural or synthetic.

As used herein, the term "Controlled release" refers to the release of an agent such as a drug from a composition or dosage form in which the agent is released according to a desired profile over an extended period of time. Controlled release profiles include, for example, sustained release, prolonged release, pulsatile release, and delayed release profiles. In contrast to immediate release compositions, controlled release compositions allow delivery of an agent to a subject over an extended period of time according to a predetermined profile. Such release rates can provide therapeutically effective levels of agent for an extended period of time and thereby provide a longer period of pharmacologic or diagnostic response as compared to conventional rapid release dosage forms. Such longer periods of response provide for many inherent benefits that are not achieved with the corresponding short acting, immediate release preparations. For example, in the treatment of chronic pain, controlled release formulations are often highly preferred over conventional short-acting formulations.

Controlled release pharmaceutical compositions and dosage forms are designed to improve the delivery profile of agents, such as drugs, medicaments, active agents, diagnostic agents, or any substance to be internally administered to an animal, including humans. A controlled release composition is typically used to improve the effects of administered substances by optimizing the kinetics of delivery, thereby increasing bioavailability, convenience, and patient compliance, as well as minimizing side effects associated with inappropriate immediate release rates such as a high initial release rate and, if undesired, uneven blood or tissue levels.

The present invention provides a taste-masked pharmaceutical composition including a drug-resin complex and a highly compressible, free-flowing pharmaceutical excipient. The resin is present in an amount effective to reduce the taste of the drug in the drug resin complex by patients that is significant relative to an otherwise identical pharmaceutical composition without the resin. The highly compressible, free-flowing pharmaceutical excipient the formulation to be compressed, while allowing for rapid disintegration or breakdown by chewing in the mouth. The pharmaceutical composition includes a chewable tablet, a solid, a liquid, an orally disintegrable tablet, a gel, a tab, a powder, a gum, a lozenge or a combination thereof. The disintegratable formulations may be delivered to, and adapted for, oral, nasal, buccal, ocular, urethral, transmucosal, vaginal, topical or rectal delivery, although oral delivery is used mostly. In addition, conventional excipients such as colorants, anti-tack agents, fillers, plasticizers, pore forming agents, glossing agents, etc. can be added to the present invention.

The present invention provides a taste-masked chewable pseudoephedrine and chlorpheniramine pharmaceutical composition. The composition includes a pseudoephedrine-resin complex, a chlorpheniramine-resin complex and one or more amorphous sugars. The composition also includes a compressible, free-flowing, pharmaceutical, taste-masking excipient, wherein the highly compressible, free-flowing pharmaceutical excipient causes disintegration of the tablet and liberation of the drug-resin complex in the mouth. In some instances the resin is polistirex, polyacrilex or a combination thereof, and more specifically pseudoephedrine polistirex and chlorpheniramine polyacrilex. The amorphous sugar may be the commercially available Pharmaburst or other sugars known to the skilled artisan. However the skilled artisan will recognize that other combinations of actives, resins and sugars may be used.

The present invention also includes a taste-masked soluble chewable pseudoephedrine and chlorpheniramine pharmaceutical composition. The composition includes a pseudoephedrine-resin complex, a chlorpheniramine-resin complex, one or more amorphous sugars and a compressible, free-flowing, pharmaceutical, taste-masking excipient. The pseudoephedrine and the chlorpheniramine are slowly released when the composition is chewed. The composition becoming thixotropic when chewed but not fully dissolving for at least 10 seconds, so as to dissolve thereafter in saliva during chewing.

The present invention includes a rapidly disintegrating, taste-masked hyoscyamine pharmaceutical composition. The composition includes a hyoscyamine-resin complex, one or more amorphous sugars and a compressible, free-flowing, pharmaceutical, taste-masking excipient. The hyoscyamine is slowly released as the tablet disintegrates. In some instances the resin is polistirex, polyacrilex or a combination thereof, and more specifically hyoscyamine polistirex. The amorphous sugar may be the commercially available Pharmaburst or other sugar known to the skilled artisan.

The present invention also includes a rapidly disintegrating, taste-masked hyoscyamine pharmaceutical composition. The composition includes a hyoscyamine-resin complex and one or more amorphous sugars. The hyoscyamine is slowly released when the composition is chewed, the composition becoming thixotropic when chewed but not fully dissolving for at least 10 seconds when chewed, and the composition slowly dissolves when the composition is chewed, so as to completely dissociate thereafter once swallowed. Alternatively, the active agent is slowly released when the composition is chewed, the composition becoming thixotropic when chewed but not fully dissolving for at least 10 seconds when chewed, and the composition slowly dissolves when the composition is chewed; however the remaining material need not be swallowed and may be discarded. The present invention may be formulated in a variety of forms including a chewable tablet, a solid, a liquid, a gel, a tab, a capsule, a disintegrating tablet, a powder, a lotion, a cream, a gum, a lozenge or combination thereof.

Generally, the drug-resin complex includes an exchange resin, e.g., cationic exchange resin. The resin may be divinylbenzene sulfonic acid cationic exchange resin, e.g., polistirex. In some embodiments the drug-resin complex includes pseudoephedrine polistirex, chlorpheniramine polistirex, hyoscyamine polistirex or a combination thereof.

The present invention includes a soluble chewable tablet including a pharmaceutically active drug-resin complex. The pharmaceutically active ingredient is slowly released when the tablet is chewed. As the tablet is chewed it becomes thixotropic but not fully dissolving for at least 30 seconds, rapidly disintegrating during chewing but preventing the release of the ionic drug until after the complex is swallowed The tablet may contain other conventional ingredients, including other fillers, which include water-soluble compressible carbohydrates such as dextrose, sucrose, mannitol, sorbitol, maltitol, xylitol, lactose, and mixtures thereof; other conventional dry binders like polyvinyl pyrrolidone and the like; sweeteners such as aspartame, acesulfame potassium, sucralose, and saccharin; and lubricants, such as magnesium stearate, stearic acid, talc, and waxes. The mixture may also incorporate pharmaceutically acceptable adjuvants, including, for example, preservatives, flavors, antioxidants, surfactants, and coloring agents.

When in the form of a chewable tablet components include all those substances which, alone or mixed with one another, behave like chewing gum for at least 5 seconds when chewed, but begin to disintegrate during this time and are then completely disintegrated and swallowed with the saliva. The range of substances include, inter alia, but not exclusively, gum arabic, tragacanth, guar gum, xanthan gum, pectins; but also dry syrups, such as, for example, dry glucose syrup and/or fructose syrup; soluble cellulose derivatives, such as, for example, sodium carboxymethylcellulose. Dry glucose syrup likewise exhibits partly rubber-like behavior on chewing.

The pharmaceutical composition of the present invention also includes an orally disintegrable composition having the amount of disintegration agent, either effervescent or noneffervescent or the combination thereof provided sufficient such that the composition provides a pleasant organoleptic sensation in the mouth of the patient. In general, the amount of effervescence disintegration agent, noneffervescent disintegration agent or both in accordance with the present invention should be sufficient to allow for the rapid and complete disintegration of the composition when orally administered. Complete disintegration of the composition does not require dissolution or disintegration of the microparticles or other discrete materials included.

The present invention may contain preservatives to prevent microbial contamination. Examples of preservatives are the alkylparabens, particularly methylparaben, propylparaben and butylparaben. The amount of preservative generally used will vary depending upon the preservative selected and may, for example, range from about 0.05% to about 15% weight/volume of the final composition. The preservative will be present in an amount from about 0.01% to about 20% weight/volume of the final composition.

In some instances the present invention may include a syrup component including glucose syrup, maltodextrin solution, swollen gelatin, but also other syrups, such as corn, sugar or invert sugar syrup. Glucose syrup can be completely or partly replaced by other concentrated carbohydrate, sugar alcohol, gelatin or similar solutions.

The present invention also includes a tablet formulation that has one or more amorphous sugars. The skilled artisan will recognize that many amorphous sugars may be used. Generally, amorphous sugar signifies a sugar which is materially amorphous or which is capable of becoming amorphous. In the process of becoming amorphous there may be states where a portion is not amorphous. Commercially, amorphous sugars such as Mannogem EZ and Pharmaburst (both available from SPI Pharma, Lewes, Del.) may be used to provide fast delivery.

The skilled artisan will recognize that other amorphous sugars and combinations of sugars may be used. Examples of amorphous sugars include glucose, lactose, maltose, sorbitol, trehalose, lactitol, fructose, polyols and the like. Polyols may be used in the present invention and function as an additive, compacting agent, filler, and/or carriers inter alia for active pharmaceutical ingredients. Polyols have sweetening properties which are comparable to those of sucrose and many polyols show a cooling effect, which is felt to be pleasant, during the dissolving process. Commonly used polyols include xylitol, mannitol, lactitol, isomalt and sorbitol.

Generally, polyols may be used in the present invention as they have a sweet taste and can be used to provide a cooling effect in the mouth. Commonly-used polyols include xylitol, mannitol, sorbitol and erythritol. However, the skilled artisan will recognize that a variety of polyols and combinations of polyols may be used. Xylitol is an odorless white crystalline powder that is comparably sweet to sucrose. The heat of solution of crystalline xylitol causes a strong cooling sensation in the mouth when the crystals dissolve. Crystalline xylitol can also change the flavor profiled. Erythritol is an odorless white crystalline powder with a clean sweet taste that is similar to sucrose. The heat of solution of crystalline erythritol also causes a strong sensory cooling feeling in the mouth like xylitol. Sorbitol is a popular bulk sweetener found in numerous food products. In addition to providing sweetness, it is an excellent humectant and texturizing agent. Mannitol is a monosaccharide polyol. Both sorbitol and mannitol are generally stable and chemically unreactive.

In addition cellulose esters such as cellulose acetate and cellulose acetate butyrate, and cellulose triacetate may be used as taste masking agents since they do not dissolve in the mouth and are tough enough to remain effectively intact during processing and normal chewing in the mouth.

Adsorption of the active ingredient onto the ion exchange resin particles to form the active agent-resin complex is a well-known technique as shown in U.S. Pat. No. 2,990,332 (relevant portions incorporated herein by reference) and demonstrated in the examples hereinbelow. In general, the active ingredient is mixed with an aqueous suspension of the resin and the complex is then dried. Adsorption of the active ingredient onto the resin is detected by a change in the pH of the reaction medium.

In accordance with the present invention the active ingredient can be any pharmaceutically active material and can also include vitamins, minerals, nutritional supplements and the like. These can include, without limitation systematically distributable pharmaceutically active materials, vitamins, minerals, dietary supplements, as well as non-systematically distributable pharmaceutically active materials. Drugs or pharmaceutically active materials may include, without limitation, antacids, analgesics, anti-inflammatories, antipyretics antibiotics, antimicrobials, laxatives, anorexics, antihistamines, antiasthmatics, antidiuretics, anti flatuents, antimigraine agents, antispasmodics, sedatives, antihyperactives, antihypertensives, tranquilizers, decongestants, beta blockers and combinations thereof.

In addition, nanoparticulate and microparticulate active agents may be used in the present invention and may include proteins, peptides, nucleotides, anti-obesity drugs, nutraceuticals, corticosteroids, elastase inhibitors, anti-fungals, oncology therapies, anti-emetics, analgesics, cardiovascular agents, anti-inflammatory agents, anthelmintics, anti-arrhythmic agents, antibiotics, anticoagulants, antidepressants, antidiabetic agents, anti epileptics, antihistamines, antihypertensive agents, antimuscarinic agents, antimycobacterial agents, antineoplastic agents, immunosuppressants, antithyroid agents, antiviral agents, anxiolytics, sedatives, astringents, beta-adrenoceptor blocking agents, blood products and substitutes, cardiac inotropic agents, contrast media, corticosteroids, cough suppressants, diagnostic agents, diagnostic imaging agents, diuretics, dopaminergics, haemostatics, immunological agents, lipid regulating agents, muscle relaxants, parasympathomimetics, parathyroid calcitonin and biphosphonates, prostaglandins, radio-pharmaceuticals, sex hormones, anti-allergic agents, stimulants and anoretics, sympathomimetics, thyroid agents, vasodilators, and xanthines.

Substrates include a powder that constitutes a finely divided (e.g., milled, micronized, nanosized, precipitated) form of an active ingredient or additive molecular aggregates or a compound aggregate of multiple components or a physical mixture of aggregates of an active ingredient and/or additives. Such substrates may be formed of various materials known in the art, such as, for example sugars (e.g., lactose, sucrose or dextrose), polysaccharides (e.g., maltodextrin or dextrates), starches, cellulosics (e.g., microcrystalline cellulose or microcrystalline cellulose/sodium carboxymethyl cellulose), inorganics (e.g., dicalcium phosphate, hydroxyapitite, tricalcium phosphate, talc, or titania) and polyols (e.g., mannitol, xylitol, sorbitol or cyclodextrin).

Flavoring agents that may be used in the present invention include, and are not limited to, natural flavors, natural fruit flavors, artificial flavors, artificial fruit flavors, flavor enhancers or mixtures thereof. Natural flavors, artificial flavors or mixtures thereof include, and are not limited to, mint (e.g., peppermint or spearmint), lemon, lime, orange, strawberry, menthol, cinnamon, vanilla, artificial vanilla, chocolate, artificial chocolate or bubblegum. Natural fruit flavors, artificial fruit flavors or mixtures thereof include, and are not limited to, cherry, grape, orange, strawberry or lemon. Flavor enhancers include, and are not limited to, citric acid. Although flavoring agents are generally provided as a minor component of the taste masking composition in amounts effective to provide a palatable flavor to the liquid pharmaceutical composition, the addition of at least one flavoring agent is preferred; and, more preferably, up to two flavoring agents may be employed. A flavoring agent used in the taste masking composition has a range of from about 0.01 to about 0.15 grams per 100 mL. The flavorings are generally utilized in amounts that will vary depending upon the individual flavor, and may, for example, range in amounts of about 0.01% to about 10% by weight/volume of the final composition.

Examples of sweeteners include sweetening agents, artificial sweeteners and dipeptide based sweeteners, e.g., monosaccharides, disaccharides and polysaccharides such as xylose, ribose, glucose, mannose, galactose, fructose, dextrose, sucrose, sugar, maltose, partially hydrolyzed starch, or corn syrup solids and sugar alcohols such as sorbitol, xylitol, mannitol, saccharin salts, i.e., sodium, or calcium saccharin salts, cyclamate salts, acesulfam-K, ammonium glycyrrhizinate, dipotassium glycyrrhizinate and the free acid form of saccharin L-aspartylphenylalanine methyl ester and mixtures thereof.

Generally, the sweetener will be present in an amount corresponding to about 1 to 60% weight/volume of the total composition, the amount depending in part upon whether other sweetener ingredients are present and the level of sweetness desired. Typically sugar is used it is present from about 10% to about 50% w/v of the composition. It will be appreciated that combinations of sweeteners can be used. The sweetening agents, when used, may also be used alone or in combination with each other. When an artificial sweetness enhancer is used it may be present in an amount from about 0.05% to about 15% weight/volume of the final composition.

The colorants useful in the present invention include pigments such as titanium dioxide, that may be incorporated in amounts of up to about 10% by weight/volume. The colorants may include other dyes suitable for food, drug and cosmetic applications, and known as F.D. & C. dyes and the like. The materials acceptable for the foregoing spectrum of use may be water-soluble. Illustrative examples include indigoid dye, known as F.D. & C. Blue No. 2, which is the disodium salt of 5,5'-indigotindisulfonic acid. Similarly, the dye known as F.D. & C. Green No. 1, includes a triphenylmethane dye and is the monosodium salt of 4-[4-Nethyl-p-sulfobenzylamino) diphenylmethylene]-[1-(N-ethyl-N-p-sulfoniumbenzyl)-2, 5-cyclohexadienimine].

Examples of organic acids for use with the formulations include, e.g., citric acid, tartaric acid, succinic acid, malic acid, fumaric acid, hydroxybenzoic acid and the like. The hydroxybenzoic acids include paraben esters of p-hydroxybenzoic acid (e.g., methyl paraben, ethyl paraben, propyl paraben, butyl paraben and benzyl paraben). Salts of drugs where the anion of the salt is acidic, such as acetate, hydrochloride, hydrobromide, sulfate, succinate, citrate, and the like, may be used to produce immediate disintegration and dissolution of the porous particle. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards. The interaction of an acidic component with, e.g., a porous particle of, for example, calcium hydrogen phosphate, in the presence of water from gastric fluids accelerates dissolution of the particle at a greater rate than gastric fluid alone, producing a more rapid and complete release of the liquid, active agent formulation into the environment of use. Alternatively, alkaline components or salts of drugs may be used if the cation of the salt is alkaline such as choline may be incorporated into the liquid, active agent formulation to promote rapid and complete dissolution of a porous particle which is soluble or swells at elevated pH. Such a particle may be formed, e.g., of poly(methacrylic acid-methyl methacrylate) 1:2 available commercially as Eudragit 5100 (Rohm America, Sommerset, N.J.).

Other additives conventionally used in pharmaceutical compositions may be included, which are well known in the art. Such additives include, e.g., anti-adherents (e.g, anti-sticking agents, glidants, flow promoters, lubricants) such as talc, magnesium stearate, fumed silica), micronized silica, polyethylene glycols, surfactants, waxes, stearic acid, stearic acid salts, stearic acid derivatives, starch, hydrogenated vegetable oils, sodium benzoate, sodium acetate, leucine, PEG-4000 and magnesium lauryl sulfate. The present invention includes purified, hydrated, magnesium silicate (i.e., talc) which is widely used in oral solid dosage forms as a lubricant and diluent.

Pharmaceutical compositions according to the invention may also include one or more binding agents, filling agents, lubricating agents, suspending agents, sweeteners, flavoring agents, preservatives, buffers, wetting agents, disintegrants, effervescent agents, and other excipients. Such components are known to the skilled artisan.

Examples of filling agents include lactose monohydrate, lactose anhydrous, and various starches. Examples of binding agents include various celluloses and cross-linked polyvinylpyrrolidone, microcrystalline cellulose, microcrystalline cellulose, and silicized microcrystalline cellulose. Generally, suitable lubricants, including agents that act on the flowability of the powder to be compressed, are colloidal silicon dioxide, talc, stearic acid, magnesium stearate, calcium stearate, and silica gel.

Examples of preservatives include sorbates, and parabens, e.g., potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quarternary compounds such as benzalkoniurn chloride. In addition suitable diluents include pharmaceutically acceptable inert fillers, such as microcrystalline cellulose, lactose, dibasic calcium phosphate, saccharides, and/or mixtures of any of the foregoing.

The present invention includes disintegrants which include lightly crosslinked polyvinyl pyrrolidone, corn starch, potato starch, maize starch, and modified starches, croscarmellose sodium, cross-povidone, sodium starch glycolate, and mixtures thereof. Some embodiments of the present invention are in the form of effervescent compositions. Examples of effervescent agents include an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the acid component of the effervescent couple may be present invention.

For certain actives it may be useful to provide buffering agents, where the acid is a pharmaceutically acceptable acid, such as hydrochloric acid, hydrobromic acid, hydriodic acid, sulfuric acid, nitric acid, boric acid, phosphoric acid, acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid and uric acid, and where the base is a pharmaceutically acceptable base, such as an amino acid, an amino acid ester, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrotalcite, magnesium aluminum hydroxide, diisopropylethylamine, ethanolamine, ethylenediamine, triethanolamine, triethylamine, triisopropanolamine, or a salt of a pharmaceutically acceptable cation and acetic acid, acrylic acid, adipic acid, alginic acid, alkanesulfonic acid, an amino acid, ascorbic acid, benzoic acid, boric acid, butyric acid, carbonic acid, citric acid, a fatty acid, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, and uric acid. The buffer include acids and their base salts for example, citric acid (e.g., citric acid anhydrous), tartaric acid, malic acid, phosphoric acid and the like and their respective salts.

The present invention may also include one or more binders. The choice of binder for a given application may also be determined readily by those skilled in the art. Generally, the binder must be capable of wetting the surfaces of the particle being pelletized or granulated. In general, binders must have sufficient wet strength to allow agglomerates to be handled and sufficient dry strength to make them suitable for their intended purposes. Each process, however, makes use of a different system of forces and may require a different agglomerate strength. The final selection of the binder is made generally based on the type of equipment used. Factors that affect the equipment and binder choices include: the size and size distribution of pellets, bulk density, strength and flow properties. Other factors that affect the performance of the pellets, which may be adjusted by one skilled in the art by the inclusion of additives, choice of equipment and processing conditions.

The present invention may also include one or more coolants that will contribute a cooling sensation to products in which it is found without the unwanted harshness or flavor characteristics. Generally, coolants are compounds that provide a physiological cooling effect on the skin or on the mucous membranes of the body, particularly the mucous membranes of the nose and bronchial tract. For example, Menthol is well known for its physiological cooling effect on the skin and mucous membranes of the mouth. The "cooling" effect of menthol is a physiological effect due to the direct action of menthol on the nerve endings of the human body responsible for the detection of hot or cold and is not due to latent heat of evaporation. It is believed that the menthol acts as a direct stimulus on the cold receptors at the nerve endings, which in turn stimulate the central nervous system. In addition, menthol is a major constituent of oil of peppermint and may function as a flavoring as well. Since many of the physiological cooling agents do not have their own perceptible flavor they can be combined with other types of flavors to offer new and unique advantages.

Physiological cooling agents that may be used in the present invention include menthol, menthone glycerol ketal, menthyl lactate, N-ethyl-p-menthane-3-carboxamide, 3-1-menthoxypropane-1,2,diol, 3-substituted-P-menthanes, N-substituted-P-menthane-3-carboxamides and 3-1-menthoxypropane-1,2-diol, 3-1-menthoxypropane-1,2-diol, a ketal combined with another coolant (e.g., menthol or carboxamides), physiological cooling agents and reduced menthol, menthone ketals, menthone glycerol ketals, cyclodextrin complex with physiological cooling agents, ketoesters of menthol, sulphoxides and sulphones, acyclic carboxamides, menthyl lactate, cyclohexanamides, carbonic acids having free polar groups, acyclic secondary and tertiary alkanols, menthyl succinate and carboxamides, alpha-oxy(oxo)mercaptan alkanes, acyclic sulphonamides and sulphinamides, substituted p-menthane-3-carboxamides, substituted cyclohexanamides, alkyl substituted alicyclic carboxylic acids, alkyl substituted alicyclic esters, alkyl substituted alicyclic amides, 3-substituted p-menthanes, p-menthane-3-carboxylates, N-acetylglycine menthyl ester, L-menthyl-3-hydroxybutyrate, 2-isopropenyl-5-methylcyclohexanol, bicyclic acids, esters, amides and substituted menthanols, trialkyl-substituted cyclohexane carboxamides, cyclic and acyclic amides, ureas and sulphonamides, p-menthane carboxamide physiological cooling agent with menthol, 3-I-menthoxypropane-1,2-diol, N-substituted p-menthane carboxamides and menthol, cyclohexanol derivatives, substituted p-menthanes, substituted p-menthane-carboxamides (e.g., N-ethyl-p-menthane-3-carboxamide), acyclic darboxamides, substituted cyclohexanamides, substituted cyclohexane carboxamides, substituted ureas and sulphonamides, and substituted menthanols, hydroxymethyl and hydroxyethyl derivatives of p-menthane, menthyl succinate, 2-mercapto-cyclo-decanone, 2-isopropanyl-5-methylcyclohexanol, hydroxycarboxylic acids with 2-6 carbon atoms, menthone glycerol ketals, 3-I-menthoxypropane-1,2-dial, menthyl lactate, substituted p-menthane carboxamides (PMC), N-ethyl-p-menthane-3-carboxamide, acyclic carboxamides (AC), N-2, 3-trimethyl-2-isopropyl butanamide, N-ethyl-2,3-dimethyl-2-isopropyl butanamide, N, 2,3-trimethyl-2-isopropyl butanamide, menthone glycerol ketal (MGK), menthyl lactate (ML), menthyl succinate (MS), 3-I-menthoxypropane-1, 2-diol (TCA). Physiological cooling agents may generally be of the chemical classification of ketone, hemi ketal, ketal, acetal, or hemiacetal.

Stearic acid is commonly used in the pharmaceutical industry primarily as a lubricant for tablets and capsules. It is typically used in a concentration of 1% to 10% when used as a tablet lubricant. Stearic acid is described as a mixture of stearic acid and palmitic acid. The content of stearic acid is not less than about 10% and the sum of the two acids is not less than about 90.0%. Stearic acid is used as an emulsifying agent; solubilizing agent; tablet and capsule lubricant. The purpose in this formulation is that of a lubricant of the gauifenesin so that an adequate plug can be produced and delivered through the dosing disk without excessive wear.

Suitable excipients are those used commonly to facilitate the processes involving the preparation of the solid carrier, the encapsulation coating, or the pharmaceutical dosage form. These processes include agglomeration, air suspension chilling, air suspension drying, balling, coacervation, comminution, compression, pelletization, cryopelletization, extrusion, granulation, homogenization, inclusion complexation, lyophilization, nanoencapsulation, melting, mixing, molding, pan coating, solvent dehydration, sonication, spheronization, spray chilling, spray congealing, spray drying, or other processes known in the art. The excipients may also be precoated or encapsulated, as are well known in the art.

The excipient in the form of a hydrate may be selected from organic compounds such as dextrose monohydrate, maltodextrin, lactose monohydrate, dextrin, and citric acid monohydrate, as well as inorganic compounds including dibasic calcium phosphate dihydrate, dibasic sodium phosphate dihydrate, dibasic sodium phosphate heptahydrate, dibasic sodium phosphate dodecahydrate, monobasic sodium phosphate monohydrate, and monobasic sodium phosphate dihydrate. Preferably, the excipient in the form of a hydrate is an organic compound, more preferably dextrose monohydrate.

The present invention may include calcium stearate and/or magnesium stearate which are primarily used in pharmaceutical formulations as a lubricant in tablet and capsule manufacture. Calcium stearate has good anti-adherent and lubricant properties. Maltodextrin is used in tablet formulations as a binder and diluent in both direct compression and wet granulation process. Maltodextrin appears to have no adverse effects on the rate of tablet dissolution. As a binder it is typically used in concentrations of 1% to 25%.

The pharmaceutical compositions of the present invention may include optionally one or more solubilizers, i.e., additives to increase the solubility of the pharmaceutical active ingredient or other composition components in the solid carrier. It has been recognized by the present inventors that guaifenesin, in fact, acts as a solubilizer for phenylephrine, and is used as such in the examples provided herein. Other solubilizers are known in the art. Mixtures of solubilizers are also within the scope of the invention and are readily available from standard commercial sources.

The amount of solubilizer that may be included in compositions of the present invention is not particularly limited. Of course, when such compositions are administered to a patient, the amount of a given solubilizer is limited to a bioacceptable amount, which is readily determined by one of skill in the art. In some circumstances, it may be advantageous to include amounts of solubilizers far in excess of bioacceptable amounts, for example, to maximize the concentration of active ingredient, with excess solubilizer removed prior to providing the composition to a patient using conventional techniques, such as distillation or evaporation.

In some formulations additives may also include chelating agents (e.g., EDTA and EDTA salts); colorants or opaquants (e.g., titanium dioxide, food dyes, lakes, natural vegetable colorants, iron oxides, silicates, sulfates, magnesium hydroxide and aluminum hydroxide); coolants (e.g., trichloroethane, trichloroethylene, dichloromethane, fluorotrichloromethane); cryoprotectants (e.g., trehelose, phosphates, citric acid, tartaric acid, gelatin, dextran and mannitol); and diluents or fillers (e.g., lactose, mannitol, talc, magnesium stearate, sodium chloride, potassium chloride, citric acid, spray-dried lactose, hydrolyzed starches, directly compressible starch, microcrystalline cellulose, cellulosics, sorbitol, sucrose, sucrose-based materials, calcium sulfate, dibasic calcium phosphate and dextrose). Yet other additives may include disintegrants or super disintegrants; hydrogen bonding agents, such as magnesium oxide; flavorants or desensitizers.

The present invention may also include one or more surface stabilizer selected from the group consisting of cetyl pyridinium chloride, gelatin, casein, phosphatides, dextran, glycerol, gum acacia, cholesterol, tragacanth, stearic acid, stearic acid esters and salts, calcium stearate, glycerol monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, dodecyl trimethyl ammonium bromide, polyoxyethylene stearates, colloidal silicon dioxide, phosphates, sodium dodecylsulfate, carboxymethylcellulose calcium, hydroxypropyl celluloses, hydroxypropyl methylcellulose, carboxymethylcellulose sodium, methylcell ulose, hydroxyethylcellulose, hydroxypropyl methyl-cellulose phthalate, noncrystalline cellulose, magnesium aluminum silicate, triethanolamine, polyvinyl alcohol, polyvinylpyrrolidone, 4-(1,1,3,3-tetramethylbutyl)-phenol polymer with ethylene oxide and formaldehyde, poloxamers, poloxamines, a charged phospholipid, dimyristoyl phophatidyl glycerol, dioctylsulfosuccinate, dialkylesters of sodium sulfosuccinic acid, sodium lauryl sulfate, alkyl aryl polyether sulfonates, mixtures of sucrose stearate and sucrose distearate, triblock copolymers of the structure: -(-PEO)-(-PBO-)-(-PEO-)-, p-sononylphenoxypoly-(glycidol), decanoyl-N-methylglucamide; n-decyl β-D-glucopyranoside, n-decyl β-D-maltopyranoside, n-dodecyl β-D-glucopyranoside, n-dodecyl β-D-maltoside, heptanoyl-N-methylglucamide, n-heptyl-β-D-glucopyranoside, n-heptyl β-D-thioducoside, n-hexyl β-D-glucopyranoside, nonanoyl-N-methylglucamide, n-noyl β-D-glucopyranoside, octanoyl-N-methylglucamide, n-octyl-β-D-glucopyranoside. octyl β-D-thioglucopyranoside, lysozyme, a PEG derivatized phospholipid, PEG derivatized cholesterol, a PEG derivatized cholesterol derivative, PEG derivatized vitamin A, PEG derivatized vitamin E, and random copolymers of vinyl acetate and vinyl pyrrolidone, biopolymers, polysaccharides, cellulosics, cationic lipids, benzalkonium chloride, sulfonium compounds, phosphonium compounds, quartemary ammonium compounds, benzyl-di(2-chloroethyl)ethylammonium bromide, coconut trimethyl ammonium chloride, coconut trimethyl ammonium bromide, coconut methyl dihydroxyethyl ammonium chloride, coconut methyl dihydroxyethyl ammonium bromide, decyl triethyl ammonium chloride, decyl dimethyl hydroxyethyl ammonium chloride, decyl dimethyl hydroxyethyl ammonium chloride bromide, $C_{12-15}$ dimethyl hydroxyethyl ammonium chloride, $C_{12-15}$ dimethyl hydroxyethyl ammonium chloride bromide, coconut dimethyl hydroxyethyl ammonium chloride, coconut dimethyl hydroxyethyl ammonium bromide, myristyl trimethyl ammonium methyl sulphate, lauryl dimethyl benzyl ammonium chloride, lauryl dimethyl benzyl ammonium bromide, lauryl dimethyl (ethenoxy)4 ammonium chloride, lauryl dimethyl (ethenoxy)4 ammonium bromide, N-alkyl ($C_{12-18}$)dimethylbenzyl ammonium chloride, N-alkyl ($C_{14-18}$)dimethyl-benzyl ammonium chloride, N-tetradecylidmethylbenzyl ammonium chloride monohydrate, dimethyl didecyl ammonium chloride, N-alkyl and ($C_{12-14}$) dimethyl 1-napthylmethyl ammonium chloride, trimethylammonium halide, alkyl-trimethylammonium salts, dialkyl-dimethylammonium salts, lauryl trimethyl ammonium chloride, ethoxylated alkyamidoalkyldialkylammonium salt, an ethoxylated trialkyl ammonium salt, dialkylbenzene dialkylammonium chloride, N-diclecyldimethyl ammonium chloride, N-tetradecyldimethylbenzyl ammonium, chloride monohydrate, N-alkyl($C_{12-14}$) dimethyl 1-naphthylmethyl ammonium chloride, dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, $C_{12}$ trimethyl ammonium bromides, $C_{15}$ trimethyl ammonium bromides, $C_{17}$ trimethyl ammonium bromides, dodecylbenzyl triethyl ammonium chloride, poly-diallyldimethylammonium chloride, dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride, tetrabutylammonium bromide, benzyl trirnethylammonium bromide, choline esters, benzalkonium chloride, stearalkonium chloride compounds, cetyl pyridinium bromide, cetyl pyridinium chloride, halide salts of quaternized polyoxyethylalkylamines, alkyl pyridinium salts; amines, amine salts, amine oxides, imide azolinium salts, protonated quaternary acrylamides, methylated quaternary polymers, cationic guar, polymethylmethacrylate trimethylammonium bromide, polyvinylpyrrolidone-2-dimethylaminoethyl methacrylate dimethyl sulfate, hexadecyltrimethyl ammonium bromide, poly (2-methacryloxyethyltrimethylammonium bromide), poly(N-vinyl pyrrolidone/2-dimethylaminoethyl methacrylate) dimethylsulphate quarternary and poly(2-methylacryloxyamidopropyltrimethylammonium chloride).

Pelletizers are generally classified based on the angle of their axis as a horizontal drum or an inclined dish pelletizer. Rotary fluidized granulators may also be used for pelletization. A standard fluidized drier bowl may be replaced with a rotating plate as an air distributor. For granulation, a binder liquid is sprayed from via one or two binary nozzles located axially to the rotational movement of the powder bed. The granulation results in rounding of the granules to approximately spherical pellets. Such balling or agitation techniques are generally influenced by operating conditions, e.g., the bridging/binding liquid requirements, the residence time of the material in the pelletizer, the speed and angle of inclination of the pelletizer, the amount of material fed to the pelletizer and the choice and levels of binder, etc. Those skilled in the art may adjust readily such factors to produce a satisfactory product.

A pelletization process typically involves preparing a molten solution of the composition of the solid carrier or a dispersion of the composition of the solid carrier solubilized or suspended in an aqueous medium, an organic solvent, a supercritical fluid, or a mixture thereof. Such solution or dispersion is then passed through a certain opening to achieve the desired shape, size, and other properties. Similarly, appropriate drying processes may be used to control the level of the residual dispersing medium, if necessary. The processes described above, the combination of the processes, or the modification of the processes are well know in the art.

A tablet may be made by compression or molding, optionally with one or more accessory ingredients. Compressed tablets may be prepared by compressing, in a suitable machine, the therapeutic ingredient in a free-flowing form such as a powder or granules, optionally mixed with a binder, lubricant, inert diluent, preservative, surface therapeutic or dispersing agent. Molded tablets may be made by molding, in a suitable machine, a mixture of the powdered compound moistened with an inert liquid diluent. The tablets may be optionally coated or scored and may be formulated so as to provide a slow or controlled release of the therapeutic ingredient therein.

The tablet may be made in any manner, and a variety of tableting methods are known in the art. Conventional methods for tablet production include direct compression ("dry blending"), dry granulation followed by compression, and wet granulation followed by drying and compression. Other methods include the use of compacting roller technology, e.g., a chilsonator (e.g., a dry granulation/roll compactor roller press system), drop roller, molding, casting, or extrusion technologies. All of these methods are well known in the art. The tablets are formed by the direct compression method, which involves directly compacting a blend of the active ingredient, the excipient in the form of a hydrate, the water-swellable excipient, and any other appropriate optional ingredients. After blending, a pre-determined volume of particles is filled into a die cavity of a rotary tablet press, which continuously rotates as part of a "die table" from the filling position to a compaction position. The particles are compacted between an upper punch and a lower punch to an ejection position, at which the resulting tablet is pushed from the die cavity by the lower punch and guided to an ejection chute by a stationary "take-off" bar.

Two examples of the present invention include a chewable tablet with the following formulations:

Example I

| First active ingredient polistirex | 100.00 mg |
| Second active ingredient polistirex | 15.00 mg |
| Pharamaburst | 170.00 mg |
| Sorbitol | 100.00 mg |
| Sweetener | 25.00 mg |
| Xylisorb | 30.00 mg |
| Citric acid | 10.00 mg |
| Flavor | 7.50 mg |
| Dye | 2.50 mg |
| Talc | 40.00 mg |
| Steric acid | 10.00 mg |

Example II

| Pseudoephedrine polistrex | 99.70 mg |
| Chlorpheniramine polyacrilex | 14.70 mg |
| Pharamaburst | 170.00 mg |
| Sorbitol | 100.00 mg |
| Aspertame | 25.00 mg |
| Xylisorb | 30.00 mg |
| Citric acid | 10.00 mg |
| Grape Flavor | 7.50 mg |
| Purple Lake Blend | 2.50 mg |
| Talc | 40.00 mg |
| Steric acid | 10.00 mg |

Below is a list of actual assay results for one example of the present invention with the composition listed as formula II above. The dissolution profile for the release of pseudoephedrine and chlorpheniramine are shown in Table 1, below.

TABLE 1

|  | 30 min (%) | 1 Hr (%) | 3 Hr (%) | 8 Hr (%) |
| --- | --- | --- | --- | --- |
| Chlorpheniramine | 35.1 | 42.7 | 51.6 | 60.8 |
| Pseudoephedrine | 27.6 | 37.8 | 59.4 | 82.0 |

Based on assay and dissolution profile 35.1% of the chlorpheniramine is released within 30 minutes. The release of chlorpheniramine at 1 hour is about 42.7%. The release profile after 3 hours and 8 hours demonstrate a release of 51.6% and 60.8% respectively. The dissolution profile also shows that 26.7% the pseudoephedrine is released within 30 minutes. The release of pseudoephedrine at 1 hour is about 37.8%. The release profile after 3 hours and 8 hours demonstrate a release of 59.4% and 82.0% respectively.

Example III

| Pseudoephedrine polistrex | 102.92 mg |
| --- | --- |
| Chlorpheniramine polyacrilex | 15.11 mg |
| Pharamaburst | 170.00 mg |
| Sorbitol | 86.97 mg |
| Aspartame | 25.00 mg |
| Xylisorb | 30.00 mg |
| Citric acid | 10.00 mg |
| Grape Flavor | 7.50 mg |
| Purple Lake Blend | 2.50 mg |
| Talc | 40.00 mg |
| Steric acid | 10.00 mg |

Below is a list of assay results for one example of the present invention with the composition listed as formula II above. The dissolution profile for the release of pseudoephedrine and chlorpheniramine are shown in Table 2, below.

TABLE 2

|  | 30 min (%) | 1 Hr (%) | 3 Hr (%) | 8 Hr (%) |
| --- | --- | --- | --- | --- |
| Chlorpheniramine | 36.4 | 42.1 | 51.0 | 60.7 |
| Pseudoephedrine | 27.0 | 36.3 | 53.0 | 78.4 |

Based on assay and dissolution profile 36.4% of the chlorpheniramine is released within 30 minutes. The release of chlorpheniramine at 1 hour is about 42.1%. The release profile after 3 hours and 8 hours demonstrate a release of 51.0% and 60.7% respectively. The dissolution profile also shows that 27.0% of the pseudoephedrine is released within 30 minutes. The release of pseudoephedrine at 1 hour is about 36.3%. The release profile after 3 hours and 8 hours demonstrate a release of 53.0% and 78.4% respectively.

Below is a list of actual assay results for one example of the present invention with the composition listed as formula II above. The dissolution profile for the release of pseudoephedrine and chlorpheniramine are shown in Table 3, below.

TABLE 3

|  | 30 min (%) | 1 Hr (%) | 3 Hr (%) | 8 Hr (%) |
| --- | --- | --- | --- | --- |
| Chlorpheniramine | 40.1 | 45.1 | 53.3 | 62.1 |
| Pseudoephedrine | 29.2 | 39.7 | 61.2 | 85.2 |

Based on assay and dissolution profile 29.2% of the pseudoephedrine is released within 30 minutes. The release of pseudoephedrine at 1 hour is about 39.7%. The release profile after 3 hours and 8 hours demonstrate a release of 61.2% and 85.2% respectively. The dissolution profile also shows that 40.1% of the chlorpheniramine is released within 30 minutes. The release of chlorpheniramine at 1 hour is about 45.1%. The release profile after 3 hours and 8 hours demonstrate a release of 53.3% and 62.1% respectively.

In addition the composition may be in the form of a capsule. Below is a list of actual assay results for one example of the present invention when in the form of a capsule. The dissolution profile for the release of pseudoephedrine and chlorpheniramine are shown in Table 4, below.

TABLE 4

| Capsules | 90 min (%) | 3 Hr (%) | 6 Hr (%) | 12 Hr (%) |
| --- | --- | --- | --- | --- |
| Pseudoephedrine | 34.8 | 54.1 | 75.4 | 91.7 |
| Chlorpheniramine | 21.9 | 35.4 | 55.2 | 78.6 |

Based on assay and dissolution profile of the capsule 34.8% of the pseudoephedrine is released within 90 minutes. The release of pseudoephedrine at 3 hour is about 54.1%. The release profile after 6 hours and 12 hours demonstrate a release of 75.4% and 91.7% respectively. The dissolution profile also shows that 21.9% of the chlorpheniramine is released within 90 minutes. The release of chlorpheniramine at 3 hour is about 35.4%. The release profile after 6 hours and 12 hours demonstrate a release of 55.2% and 78.6% respectively.

Generally, sorbitol is highly compressible and binds other tablet ingredients and may be used in pharmaceutical tablets, powders, and sachets. It may be used in direct compression tableting have particle size distributions that make them free-flowing. The particle size is controlled to optimize the flow characteristics of the granulations in modern tablet presses. Sorbitol increases the strength and integrity of a pharmaceutical tablet. The skill artisan will recognize that other substances may be used in place of sorbitol or in addition to sorbitol.

Example IV

| Pseudoephedrine polistrex | 102.92 mg |
| --- | --- |
| Chlorpheniramine polyacrilex | 15.11 mg |
| Pharamaburst | 170.00 mg |
| Sorbitol | 86.97 mg |
| Aspartame | 25.00 mg |
| Xylisorb | 30.00 mg |
| Citric acid | 10.00 mg |
| Grape Flavor | 7.50 mg |
| Purple Lake Blend | 2.50 mg |
| Talc | 40.00 mg |
| Steric acid | 10.00 mg |

Example V

| Active ingredient polistrex | 0.33 mg |
| --- | --- |
| Amorphous sugar | 150.00 mg |
| Excipient/binder | 10.00 mg |
| Sweetener | 5.00 mg |
| Coolant | 2.67 mg |
| Flavor | 6.00 mg |
| Dye | 0.50 mg |
| Talc | 30.00 mg |
| Steric acid | 5.00 mg |

Example VI

| | |
|---|---|
| Hyoscyamine polistirex | 0.33 mg |
| Pharmaburst | 150.00 mg |
| Povidone | 10.00 mg |
| Aspertame | 5.00 mg |
| Coolant | 2.67 mg |
| Peppermint Flavor | 6.00 mg |
| Lake Blend Lt Green | 0.50 mg |
| Talc | 30.00 mg |
| Steric acid | 5.00 mg |

Example VII

| | |
|---|---|
| Hyoscyamine polistirex | 0.33 mg |
| Mannogem ™ EZ | 150.00 mg |
| Povidone | 10.00 mg |
| Aspertame | 5.00 mg |
| Coolant | 2.67 mg |
| Peppermint Flavor | 6.00 mg |
| Lake Blend Lt Green | 0.50 mg |
| Talc | 30.00 mg |
| Steric acid | 5.00 mg |

When formulated with microparticles or nanoparticles, the one or more actives the release profile can easily be adapted by adding, e.g., a hard or soft gelatin coating, a starch coating, a resin or polymer coating and/or a cellulosic coating. Although not limited to microparticles or nanoparticles such dosage forms may be further coated with, for example, a seal coating, an enteric coating, an extended release coating, or a targeted delayed release coating. The term "enteric coating" as used herein relates to a mixture of pharmaceutically acceptable excipients that is applied to, combined with, mixed with or otherwise added to the carrier or composition. The coating may be applied to an active that is compressed, molded or extruded and may also include: gelatin, and/or pellets, beads, granules or particles of the carrier or composition. The coating may be applied through an aqueous dispersion or after dissolving in appropriate solvent. The carrier may or may not be fully or partially biodegradable.

Carriers for use with the present invention include permeable and semipermeable matrices or polymers that control the release characteristics of the formulation. Such polymers include, for example, cellulose acylates, acetates, and other semi-permeable polymers as well as the selectively permeable polymers formed by the coprecipitation of a polycation and a polyanioni. The carrier of the compositions of the present invention may be a powder or a multiparticulate, such as a granule, a pellet, a bead, a spherule, a beadlet, a microcapsule, a millisphere, a nanocapsule, a nanosphere, a microsphere, a platelet, a minitablet, a tablet or a capsule. A carrier may be a finely divided (e.g., milled, micronized, nanosized, precipitated) form of a matrix on which the active ingredient is disposed. Such matrix may be formed of various materials known in the art, such as, for example: sugars, such as lactose, sucrose or dextrose; polysaccharides, such as maltodextrin or dextrates; starches; cellulosics, such as microcrystalline cellulose or microcrystalline cellulose/sodium carboxymethyl cellulose; inorganics, such as dicalcium phosphate, hydroxyapitite, tricalcium phosphate, talc, or titania; and polyols, such as mannitol, xylitol, sorbitol or cyclodextrin. It should be emphasized that a substrate need not be a solid material, although often it will be a solid.

Other carriers for use with the present invention include, e.g., starch, modified starch, and starch derivatives, gums, including but not limited to xanthan gum, alginic acid, other alginates, benitoniite, veegum, agar, guar, locust bean gum, gum arabic, quince psyllium, flax seed, okra gum, arabinoglactin, pectin, tragacanth, scleroglucan, dextran, amylose, amylopectin, dextrin, etc., cross-linked polyvinylpyrrolidone, ion-exchange resins, such as potassium polymethacrylate, carrageenan (and derivatives), gum karaya, biosynthetic gum, etc. Other useful polymers include: polycarbonates (linear polyesters of carbonic acid); microporous materials (bisphenol, a microporous poly(vinyl chloride), micro-porous polyamides, microporous modacrylic copolymers, microporous styrene-acrylic and its copolymers); porous polysulfones, halogenated poly(vinylidene), polychloroethers, acetal polymers, polyesters prepared by esterification of a dicarboxylic acid or anhydride with an alkylene polyol, poly(alkylenesulfides), phenolics, polyesters, asymmetric porous polymers, cross-linked olefin polymers, hydrophilic microporous homopolymers, copolymers or interpolymers having a reduced bulk density, and other similar materials, poly(urethane), cross-linked chain-extended poly(urethane), poly(imides), poly(benzimidazoles), collodion, regenerated proteins, semi-solid cross-linked poly(vinylpyrrolidone).

Additional additives and their levels, and selection of a primary coating material or materials will depend on the following properties: resistance to dissolution and disintegration in the stomach; impermeability to gastric fluids and drug/carrier/enzyme while in the stomach; ability to dissolve or disintegrate rapidly at the target intestine site; physical and chemical stability during storage; non-toxicity; easy application as a coating (substrate friendly); and economical practicality.

The one or more active agents that are formulated in a self-stable manner using the present invention may include a wide variety of uses, not just the traditional pharmaceutical agents. Those skilled in the art will appreciate that any of these compounds may be used in the form of their pharmaceutically acceptable salt forms, e.g., carboxylic acids, with counter-ions, e.g., potassium, sodium, calcium; as ionic combinations with, e.g., resins, polymers, beads, matrices; with sugars or sugar derivatives, e.g., malate, tannate; amino acids, lipids, oils or combinations, mixtures and the like. In some embodiments, the present inventors have found that certain actives may be provided with two different salts, each of which may have a different solubility and/or release profile under, e.g., physiologic conditions. In fact, liquid formulation of present invention includes combinations of one or more of the following: immediate release, pulsatile release, controlled release, extended release, delayed release, targeted release, or targeted delayed release.

Some examples of active ingredients suitable for use in the pharmaceutical formulations and methods of the present invention include hydrophilic, lipophilic, amphiphilic or hydrophobic, and that can be solubilized, dispersed, or partially solubilized and dispersed, on or about a earlier. For example, the following example may be used for the following active agents:

Example VIII

| | |
|---|---|
| Active Agent-polistirex | 0.33 mg |
| Mannogem ™ EZ | 150.00 mg |
| Povidone | 10.00 mg |

| | |
|---|---|
| Aspertame | 5.00 mg |
| Coolant | 2.67 mg |
| Peppermint Flavor | 6.00 mg |
| Lake Blend Lt Green | 0.50 mg |
| Talc | 30.00 mg |
| Steric acid | 5.00 mg |

The active agent-carrier combination may be coated further to encapsulate the agent-carrier combination. Alternatively, an active ingredient may also be provided separately from the solid pharmaceutical composition, such as for co-administration. Such active ingredients can be any compound or mixture of compounds having therapeutic or other value when administered to an animal, particularly to a mammal, such as drugs, nutrients, cosmaceuticals, nutraceuticals, diagnostic agents, nutritional agents, and the like. The active agents of the present invention may be found in their native state; however, they will generally be provided in the form of a salt. The active agents listed below include their isomers, analogs and derivatives.

In one embodiment, the active ingredient agent is hydrophobic. Hydrophobic active ingredients are compounds with little or no water solubility. Intrinsic water solubilities for hydrophobic active ingredients are generally less than about 15% by weight. Suitable hydrophobic active ingredients are not limited by therapeutic category, and can be, for example, analgesics, anti-inflammatory agents, antihelmimthics, anti-arrhythmic agents, anti-bacterial agents, anti-viral agents, anti-coagulants, anti-depressants, anti-diabetics, anti-epileptics, anti-fungal agents, anti-gout agents, anti-hypertensive agents, anti-malariale, anti-migraine agents, anti-muscarinic agents, anti-neoplastic agents, erectile dysfunction improvement agents, immunosuppressants, anti-protozoal agents, anti-thyroid agents, anxiolytic agents, sedatives, hypnotics, neuroleptics. β-Blockers, cardiac inotropic agents, corticosteroids, diuretics, anti-parkinsonian agents, gastro-intestinal agents, histamine receptor antagonists, keratolytics, lipid regulating agents, anti-anginal agents, cox-2 inhibitors, leukotriene inhibitors, macrolides, muscle relaxants, nutritional agents, opioid analgesics, protease inhibitors, sex hormones, stimulants, muscle relaxants, anti-osteoporosis agents, anti-obesity agents, cognition enhancers, anti-urinary incontinence agents, nutritional oils, anti-benign prostate hypertrophy agents, essential fatty acids, non-essential fatty acids, and mixtures thereof. Salts, isomers and derivatives of the above-listed hydrophobic active ingredients may also be used, as well as combinations and mixtures thereof.

Other examples of suitable hydrophobic active ingredients include: acetretin, albendazole, albuterol, aminoglutethimide, amiodarone, amlodipine, amphetamine, amphotericin B, atorvastatin, atovaquone, azithromycin, baclofen, beclomethasone, benezepril, benzonatate, betamethasone, bicalutanide, budesonide, bupropion, busulfan, butenafine, calcifediol, calcipotriene, calcitriol, camptothecin, candesartan, capsaicin, carbamezepine, carotenes, celecoxib, cerivastatin, cetirizine, chlorpheniramine, cholecalciferal, cilostazol, cimetidine, cinnarizine, ciprofloxacin, cisapride, clarithromycin, clemastine, clomiphene, clomipramine, clopidogrel, codeine, coenzyme Q10, cyclobenzaprine, cyclosporin, danazol, dantrolene, dexchlorpheniramine, diclofenac, dicoumarol, digoxin, dehydroepiandrosterone, dihydroergotamine, dihydrotachysterol, dirithromycin, donezepil, efavirenz, eposartan, ergocalciferol, ergotamine, essential fatty acid sources, etodolac, etoposide, famotidine, fenofibrate, fentanyl, fexofenadine, finasteride, fluconazole, flurbiprofen, fluvastatin, fosphenytoin, frovatriptan, furazolidone, gabapentin, gemfibrozil, glibenclamide, glipizide, glyburide, glimepiride, griseofulvin, halofantrine, ibuprofen, irbesartan, irinotecan, isosorbide dinitrate, isotretinoin, itraconazole, ivermectin, ketoconazole, ketorolac, lamotrigine, lansoprazole, leflunomide, lisinopril, loperamide, loratadine, lovastatin, L-thryroxine, lutein, lycopene, medroxyprogesterone, mifepristone, mefloquine, megestrol acetate, methadone, methoxsalen, metronidazole, miconazole, midazolam, miglitol, minoxidil, mitoxantrone, montelukast, nabumetone, nalbuphine, naratriptan, nelfinavir, nifedipine, nilsolidipine, nilutanide, nitrofurantoin, nizatidine, omeprazole, oprevelkin, oestradiol, oxaprozin, paclitaxel, paracalcitol, paroxetine, pentazocine, pioglitazone, pizofetin, pravastatin, prednisolone, probucol, progesterone, pseudoephedrine, pyridostigmine, rabeprazole, raloxifene, rofecoxib, repaglinide, rifabutine, rifapentine, rimexolone, ritanovir, rizatriptan, rosiglitazone, saquinavir, sertraline, sibutramine, sildenafil citrate, simvastatin, sirolimus, spironolactone, sumatriptan, tacrine, tacrolimus, tamoxifen, tamsulosin, targretin, tazarotene, telmisartan, teniposide, terbinafine, terazosin, tetrahydrocannabinol, tiagabine, ticlopidine, tirofibran, tizanidine, topiramate, topotecan, toremifene, tramadol, tretinoin, troglitazone, trovafloxacin, ubidecarenone, valsartan, venlafaxine, verteporfin, vigabatrin, vitamin A, vitamin D, vitamin E, vitamin K, zafirlukast, zileuton, zolmitriptan, zolpidem, and zopiclone. Of course, salts, isomers and derivatives of the above-listed hydrophobic active ingredients may also be used, as well combinations and mixtures thereof.

In other embodiments, the active ingredient is hydrophilic, however, combination of hydrophilic, hydrophobic and non-polar agents may also be used. The water solubility for hydrophilic active ingredients is generally greater than about 0.1% by weight, and typically greater than about 1% by weight. Suitable hydrophilic active ingredients include: analgesics, anti-inflammatory agents, antihelminthics, anti-arrhythmic agents, anti-bacterial agents, anti-viral agents, anti-coagulants, anti-depressants, anti-diabetics, anti-epileptics, anti-fungal agents, anti-gout agents, anti-hypertensive agents, anti-malarials, anti-migraine agents, anti-muscarinic agents, anti-neoplastic agents, erectile dysfunction improvement agents, immunosuppressants, anti-protozoal agents, anti-thyroid agents, anxiolytic agents, sedatives, hypnotics, neuroleptics, .beta.-Blockers, cardiac inotropic agents, corticosteroids, diuretics, anti-parkinsonian agents, gastro-intestinal agents, histamine receptor antagonists, keratolytics, lipid regulating agents, anti-anginal agents, cox-2 inhibitors, leukotriene inhibitors, macrolides, muscle relaxants, nutritional agents, opioid analgesics, protease inhibitors, sex hormones, stimulants, muscle relaxants, anti-osteoporosis agents, anti-obesity agents, cognition enhancers, anti-urinary incontinence agents, nutritional oils, anti-benign prostate hypertrophy agents, essential fatty acids, non-essential fatty acids, and mixtures thereof Other hydrophilic active ingredients include: a cytokine, a peptidomimetic, a peptide, a protein, a toxoid, a serum, an antibody, a vaccine, a nucleoside, a nucleotide, a portion of genetic material, a nucleic acid, or a mixture thereof. Other examples of suitable hydrophilic active ingredients include: acarbose; acyclovir; acetyl cysteine; acetylcholine chloride; alatrofloxacin; alendronate; aglucerase; amantadine hydrochloride; ambenomium; amifostine; amiloride hydrochloride; aminocaproic acid; amphotericin B; antihemophilic factor (human), antihemophilic factor (porcine); antihemophilic factor (recombinant); aprotinin; asparaginase; atenolol; atracurium besylate; atropine; azithromycin; aztreonam; BCG vaccine; bacitracin; becalennin; belladona; bepridil hydrochloride; bleomnycin sulfate; calcitonin human; calcitonin salmon; carboplatin; capecitabine; capreomycin sulfate; cefamandole nafate; cefazolin sodium; cefepime hydrochloride; cefixime; cefonicid sodium; cefoperazone; cefotetan disodium; cefotaxime; cefoxitin sodium; ceftizoxime; ceftriaxone; cefuroxime axetil; cephalexin; cephapirin sodium; cholera vaccine; chorionic gonadotropin; cidofovir; cisplatin; cladribine; clidinium bromide; clindamycin and clindamycin derivatives; ciprofloxacin; clodronate; colistimethate sodium; colistin sulfate; corticotropin; cosyntropin; cromolyn sodium; cytarabine; dalteparin sodium; danaparoid; desferrioxamine; denileukin diflitox; desmopressin; diatrizoate meglumine and diatrizoate sodium; dicyclomine; didanosine; dirithromycin; dopamine hydrochloride; dornase alpha; doxacurium chloride; doxorubicin; etidronate disodium; enalaprilat; enkephalin; enoxaparin; enoxaprin sodium; ephedrine; epinephrine; epoetin alpha; erythromycin; esmolol hydrochloride; factor IX; famciclovir; fludarabine; fluoxetine; foscamet sodium; ganciclovir; granulocyte colony stimulating factor, granulocyte-macrophage stimulating factor; growth hormones—recombinant human; growth hormone—bovine; gentamycin; glucagon; glycopyrolate; gonadotropin releasing hormone and synthetic analogs thereof; GnRH; gonadorelin; grepafloxacin; haemophilus B conjugate vaccine; Hepatitis A virus vaccine inactivated; Hepatitis B virus vaccine inactivated; heparin sodium; indinavir sulfate; influenza virus vaccine; interleukin-2; interleukin-3; insulin-human, insulin lispro; insulin procine; insulin NPH; insulin aspart; insulin glargine; insulin detemir; interferon alpha; interferon beta; ipratropium bromide; ifosfamide; Japanese encephalitis virus vaccine; lamivudine; leucovorin calcium; leuprolide acetate, levofloxacin; lincomycin and lincomycin derivatives; lobucavir; lomefloxacin; loracarbef; mannitol; is measles virus vaccine; meningococcal vaccine; menotropins; mepenzolate bromide; mesalamine; methenamine; methotrexate; methscopolamine; metfonnin hydrochloride; metoprolol; mezocillin sodium; mivacurium chloride; mumps viral vaccine; nedocromil sodium; neostigmine bromide; neostigmine methyl sulfate; neurontin; norfloxacin; octreotide acetate; ofloxacin; olpadronate; oxytocin; pamidronate disodium; pancuronium bromide; paroxetine; perfloxacin; pentamidine isethionate; pentostatin; pentoxifylline; periciclovir; pentagastrin; pentholamine mesylate; phenylalanine; physostigmine salicylate; plague vaccine; piperacillin sodium; platelet derived growth factor-human; pneumococcal vaccine polyvalent; poliovirus vaccine inactivated; poliovirus vaccine live (OPV); polymyxin B sulfate; pralidoxime chloride; pramlintide, pregabalin; propafenone; propenthaline bromide; pyridostigmine bromide; rabies vaccine; residronate; ribavarin; rimantadine hydrochloride; rotavirus vaccine; salmeterol xinafoate; sinealide; small pox vaccine; solatol; somatostatin; sparfloxacin; spectinomycin; stavudine; streptokinase; streptozocin; suxamethonium chloride; tacrine hydrochloride; terbutaline sulfate; thiopeta; ticarcillin; tiludronate; timolol; tissue type plasminogen activator; TNFR:Fc; TNK-tPA; trandolapril; trimetrexate gluconate; trospectinomycin; trovafloxacin; tubocurarine chloride; tumor necrosis factor; typhoid vaccine live; urea; urokinase; vancomycin; valacyclovir; valsartan; varicella virus vaccine live; vasopressin and vasopressin derivatives; vecuronium bromide; vinblastine; vincristine; vinorelbine; vitamin B12; warfarin sodium; yellow fever vaccine; zalcitabine; zanamivir; zolendronate; zidovudine; pharmaceutically acceptable salts, isomers and derivatives thereof; and mixtures thereof.

A wide variety of therapeutically active agents can be used in conjunction with the present invention. The therapeutically active agents (e.g. pharmaceutical agents) which may be used in the compositions of the present invention include both water soluble and water insoluble drugs. Examples of such therapeutically active agents include antihistamines (e.g., di menhydrinate, diphenhydramine, chlorpheniramine and dexchlorpheniramine maleate), analgesics (e.g., aspirin, codeine, morphine, dihydromorphone, oxycodone, etc.), non-steroidal anti-inflammatory agents (e.g., naproxyn, diclofenac, indomethacin, ibuprofen, sulindac), anti-emetics (e.g., metoclopramide), anti-epileptics (e.g., phenytoin, meprobamate and nitrezepam), vasodilators (e.g., nifedipine, papaverine, diltiazem and nicardirine), anti-tussive agents and expectorants (e.g., codeine phosphate), anti-asthmatics (e.g. theophylline), antacids, anti-spasmodics (e.g., atropine, scopolamine), antidiabetics (e.g., insulin), diuretics (e.g., ethacrynic acid, bendrofluazide), anti-thypotensives (e.g., propranolol, clonidine), antihypertensives (e.g, clonidine, methyldopa), bronchodilators (e.g., albuterol), steroids (e.g., hydrocortisone, triamcinolone, prednisone), antibiotics (e.g., tetracycline), antihemorrhoidals, hypnotics, psycho-tropics, antidiarrheals, mucolytics, sedatives, decongestants, laxatives, vitamins, stimulants (including appetite suppressants such as phenylpropanolamine), as well as salts, hydrates, and solvates of the same. The above list is not meant to be exclusive.

In certain embodiments, the therapeutically active agent include hydromorphone, oxycodone, dihydrocodeine, codeine, dihydromorphine, morphine, buprenorphine, salts, hydrates and solvates of any of the foregoing, mixtures of any of the foregoing, and the like. In other embodiments, the active agent is a locally active therapeutic agent and the environment of use may be, e.g., the gastrointestinal tract, or body cavities such as the oral cavity, periodontal pockets, surgical wounds, the rectum or vagina. The liquid formulations of the present invention may be provided orally, topically, subcutaneously, intramuscularly, intraperitoneally, intraocularly, intraossealy, nasally, urethrally, mucosally, vaginally, rectally, intradurally, epidurally and the like. The liquid formulation of the present invention may also be provided as a mist, e.g., to the deep lung (alveolarly).

Locally active pharmaceutical agents of use with the present inveention include antifungal agents (e.g., amphotericin B, clotrimazole, nystatin, ketoconazole, miconazol, etc.), antibiotic agents (penicillins, cephalosporins, erythromycin, tetracycline, aminoglycosides, etc.), antiviral agents (e.g, acyclovir, idoxuridine, etc.), breath fresheners (e.g. chlorophyll), antitussive agents (e.g., dextromethorphan hydrochloride), anti-cariogenic compounds (e.g. metallic salts of fluoride, sodium monofluorophosphate, stannous fluoride, amine fluorides), analgesic agents (e.g., methylsalicylate, salicylic acid, etc.), local anesthetics (e.g., benzocaine), oral anti-septics (e.g., chlorhexidine and salts thereof, hexylresorcinol, dequalinium chloride, cetylpyridinium chloride), anti-flammatory agents (e.g., dexamethasone, betamethasone, prednisone, prednisolone, triamcinolone, hydrocortisone, etc.), hormonal agents (oestriol), antiplaque agents (e.g, chlorhexidine and salts thereof, octenidine, and mixtures of thymol, menthol, methysalicylate, eucalyptol), acidity reducing agents (e.g., buffering agents such as potassium phosphate dibasic, calcium carbonate, sodium bicarbonate, sodium and potassium hydroxide, etc.), and tooth desensitizers (e.g., potassium nitrate). This list is not meant to be exclusive.

The examples herein include pharmaceutically active compounds useful in the practice of the present invention, e.g., antihistamines, decongestants, antitussives and/or expectorants. Other actives for use with the present invention include, but are not limited to: non-steroidal anti-inflammatory drugs (NSAIDs) and other analgesic drugs such as acetominophen and phenacetin. These materials are incorporated into the immediate or controlled release formulations of the invention in amounts governed by the desired release characteristics of the material in such excipient base and such that conventional dosages comply with applicable federal Food and Drug Administration (FDA) or other regulations.

Decongestants useful with the present invention (along with a salt form) are phenylephrine (bitartrate, tannate, HBr, HCl), phenylpropanolamine (HCl) and pseudoephedrine (HCl). Furthermore, a number of herbal and/or natural decongestants are known in the art, all of which may be used with the present invention.

Expectorants for use with the present invention include, e.g., guaifenesin, terpin hydrate, (glyceryl guaiacolate), potassium (iodide, citrate) and potassium guaicolsulfonate. Other expectorants, whether individual ingredients or combinations of ingredients may be used with the present invention. Furthermore, a number of herbal and/or natural expectorants are known in the art, all of which may be used with the present invention.

Examples of antihistamines for use with the present invention (e.g., in salt form) are chlorpheniramine (maleate), brompheniramine (maleate), dexchlorpheniramine (maleate), dexbrompheniramine (maleate), triprolidine (HCl), diphenhydramine (HCl), doxylamine (succinate), tripelennamine (HCl), cyproheptatine (HCl), bromodiphenhydramine (HCl), phenindamine (tartrate), pyrilamine (maleate, tannate) and azatadine (maleate). Antitussives that may be used with the present invention (with salt form) include: caramiphen (edisylate), dextromethorphan (HBO and codeine (phosphate, sulfate). A number of herbal and/or natural antihistamines are known in the art, all of which may be used with the present invention.

Other actives may also be included with the present invention, e.g., non-steroidal anti-inflammatory drugs (NSAIDs) such as propionic acid derivatives; acetic acid derivatives; fenamic acid derivatives; biphenylcarboxylic acid derivatives; and oxicams. Examples of propionic acid derivatives include: ibuprofen, naproxen, ketoprofen, flurbiprofen, fenoprofen, suprofen, fenbufen, and fluprofen may be mentioned as preferred compounds. Acetic acid derivatives derivatives include: tolmetin sodium, zomepirac, sulindac and indomethacin. Fenamic acid derivatives derivatives include: mefenamic acid and meclofenamate sodium. Diflunisal and flufenisal are biphenylcarboxylic acid derivatives, while oxicams include piroxicam, sudoxicam and isoxicam. Other analgesics for use with the present invention include acetominophen and phenacetin. Naproxen may be present in amounts of about 50 to about 250 milligrams per dose, however, naproxen may be used in amounts of between about 100 and about 150 milligrams per liquid dose.

Phenylephrine may be present in amounts of between about 15 and about 60 milligrams per liquid dose. Phenylephrine is generally in amounts of about 5 to about 30 milligrams per liquid dose, with half or less of that amount used in a pediatric form of the formulation. In one example of the present invention, phenylephrine is provided in the amount of about 15 mg for extended release. Phenylephrine hydrochloride is an orally effective nasal decongestant. Chemically it is (S)-3-hydroxy-α[(methylamino)methyl]benzenemethanol hydrochloride. Phenylepherine is a synthetic, optically active sympathomimetic amine that has one hydroxyl group on the benzene ring. The hydroxyl group is placed in the position meta to the aliphatic side chain. The meta position affords optimal activity and phenylepherine (neo-synephrine) replaced an older preparation, synephrine, in which the hydroxyl was in the para position.

Phenylephrine hydrochloride is available in the form of the levorotatory isomer, a white, odorless, non-hygroscopic, crystalline compound possessing a bitter taste. Phenylephrine hydrochloride has a melting point of 140-145 degrees C. and is freely soluble in water and alcohol. Decongestant compounds in the form of their free bases as well as their salts, e.g., hydrochloride, citrate, maleate, tannate, etc., are well known.

Dextromethorphan may be present in amounts of between about 5 and about 20 milligrams per liquid dose, with a general range of about 10 to about 15 milligrams. Brompheniramine may be present in amounts of between about 0.5 and about 4.0 milligrams per liquid dose with a general range of about 2.0 milligrams per liquid dose. Half or less of that amount may be used in a pediatric form of the formulation.

The present invention may also include chlorpheniramine, which is an antihistamine used to relieve, e.g., allergic rhinitis (seasonal allergy). The symptoms of allergic rhinitis include: sneezing, runny nose, itching, and watery eyes. Chlorpheniramine may also be used to treat immediate allergic reactions. Chlorpheniramine may be provided alone and in combination with other prescription or nonprescription drugs, e.g., to treat symptoms of allergy, colds, and upper respiratory infections.

The pharmaceutical composition and/or the solid carrier particles can be coated with one or more enteric coatings, seal coatings, film coatings, barrier coatings, compress coatings, fast disintegrating coatings, or enzyme degradable coatings. Multiple coatings may be applied for desired performance. Further, some actives may be provided for slow release, pulsatile release, controlled release, extended release, delayed release, targeted release, synchronized release, or targeted delayed release. For release/absorption control, solid carriers can be made of various component types and levels or thicknesses of coats, with or without an active ingredient. Such diverse solid carriers can be blended in a dosage form to achieve a desired performance. The compositions may be formulated for oral, nasal, buccal, ocular, urethral, transmucosal, vaginal, topical or rectal delivery, although oral delivery is used mostly.

The present invention may also contain a plasticizer and possibly other coating excipients such as colorants, talc, and/or magnesium stearate, which are well known in the art. Suitable plasticizers include: triethyl citrate (citroflex 2), triacetin (glyceryl triacetate), acetyl triethyl citrate, carbowax 400 (polyethylene glycol 400), diethyl phthalate, tributyl citrate, acetylated monoglycerides, glycerol, fatty acid esters, propylene glycol, and dibutyl phthalate. In particular, anionic carboxylic acrylic polymers usually will contain about 5-25% by weight of a plasticizer, especially dibutyl phthalate, polyethylene glycol, triethyl citrate and triacetin. Conventional coating techniques such as spray or pan coating are employed to apply coatings. The coating thickness must be sufficient to ensure that the oral dosage form remains intact until the desired site of topical delivery in the lower intestinal tract is reached.

It should be appreciated that there is considerable overlap between the above-listed additives in common usage, since a given additive is often classified differently by different practitioners in the field, or is commonly used for any of several different functions. Thus, the above-listed additives should be taken as merely exemplary, and not limiting, of the types of additives that can be included in compositions of the present invention. The amounts of such additives may be readily determined by one skilled in the art, according to the particular properties desired.

Additives may be include, e.g., pre-mixed propylene glycol, glycerin, citric acid, sodium benzoate, povidone (kollidon 30), sorbitol solution and the like. Flavorants, sweeteners, preservatives, bitter masking agent, thickeners and the like may also be added to the blender. In one example, the flavorants may be lemon, bubble gum, grape, wild cherry or other flavors, with sweeteners including saccharin or honey. In addition, a glycerin solution may be added in addition to water, e.g., double deionized water.

In addition the present invention may be in the form of a chewing gum formulation based on natural rubber have been widely used in the pharmaceutical industry. The advantages are the pleasant and popular dosage form and rapid, sublingual absorption of an active ingredient. When in the form of a chewing gum the present invention may include waxes, such as, for example, beeswax, solid paraffin, ozocerite, polyols, cellulose esters, pharmaceutically active materials, flavoring agents, sweeteners, colorants, stearic acid, calcium stearate, magnesium stearate, solubilizers, chelating agents, surface stabilizer, additives, or similar substances, may be used to ensure a longer chewing time, have proven particularly advantageous with regard to the chewability.

In yet another embodiment, the formulation may be a combination of a soft-gel or liquid interior coated with a more firm exterior. For example, certain agents may be provided for immediate release in a thixotropic gel in the interior of a gel or chewing-gum-like exterior.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A compressed, orally disintegrating, controlled release taste-masked pharmaceutical composition comprising:
a coated drug-ion-exchange resin complex and a directly compressible, free-flowing pharmaceutical excipient, wherein the composition effectively masks an unpalatable taste associated with delivery of the drug, wherein the coated drug-ion-exchange resin complex is coated with a controlled release coating, and wherein the directly compressible, free-flowing pharmaceutical excipient aids in the liberation of the coated drug-resin complex in the mouth through disintegration.

2. The composition of claim 1, wherein the drug in the drug-ion-exchange resin complex comprises dextromethorphan, codeine, morphine, hydrocodone, hyoscyamine, moguisteine, pseudoephedrine, chlorpheniramine, phenylpropanolamine, pharmaceutically acceptable salts of the same or combinations thereof.

3. The composition of claim 1, further comprising one or more flavorants, sweeteners, coolants, dyes, or combinations and mixtures thereof.

4. The composition of claim 1, further comprising one or more excipients, one or more binders or combinations and mixtures thereof.

5. The composition of claim 1, wherein the coated drug-ion-exchange resin complex comprises polistirex, polacrilex or combinations thereof.

6. The composition of claim 1, wherein the composition comprises pseudoephedrine polistirex and chlorpheniramine polacrilex.

7. The composition of claim 1, wherein the resin in the coated drug-ion-exchange resin complex comprises one or more cationic exchange resins.

8. The composition of claim 1, wherein the coated drug-ion-exchange resin complex comprises a divinylbenzene sulfonic acid cationic exchange resin.

9. The composition of claim 1, wherein the composition comprises a hardness of between about 5 and about 15 kPa.

10. The composition of claim 1, wherein the composition has at least about 20 percent better mouth-feel.

11. The composition of claim 1, wherein the coated drug-ion-exchange resin complex controlled release coating comprises a diffusion barrier coating.

12. The composition of claim 11, wherein the diffusion barrier coating is a time release coating.

13. A compressed, orally disintegrating, controlled release taste-masked hyoscyamine pharmaceutical composition according to claim 1 comprising:
a coated hyoscyamine-ion-exchange resin complex; and
a directly compressible, free-flowing pharmaceutical excipient that aids in the liberation of the coated hyoscyamine-ion-exchange resin complex in the mouth through disintegration.

14. The composition of claim 13, further comprising one or more flavorants, sweeteners, coolants, dyes, or combinations and mixtures thereof.

15. The composition of claim 13, further comprising one or more excipients, one or more binders or combinations and mixtures thereof.

16. The composition of claim 1, wherein the directly compressible, free-flowing pharmaceutical excipient comprises a water-soluble compressible carbohydrate.

17. The composition of claim 1, further comprising one or more amorphous sugars.

18. The composition of claim 1, further comprising a plasticizer.

19. The composition of claim 1, wherein said controlled release coating comprises a delayed release coating.

20. The composition of claim 19, wherein the drug in said drug-ion-exchange resin complex comprises an analgesic drug, anti-inflammatory drug, central nervous system agent, anti-hypertensive drug, or an anti-hyperactive drug.

21. The composition of claim 20, wherein the drug in said drug-ion-exchange resin complex comprises an anti-hyperactive drug.

22. The composition of claim 19, wherein the drug in said drug-ion-exchange resin complex comprises amphetamine.

23. The composition of claim 1, wherein the drug in said drug-ion-exchange resin complex comprises an analgesic drug, anti-inflammatory drug, central nervous system agent, anti-hypertensive drug, or an anti-hyperactive drug.

24. The composition of claim 23, wherein the drug in said drug-ion-exchange resin complex comprises an anti-hyperactive drug.

25. The composition of claim 1, wherein the drug in said drug-ion-exchange resin complex comprises amphetamine.

* * * * *